United States Patent
Ono et al.

(10) Patent No.: US 7,618,416 B2
(45) Date of Patent: Nov. 17, 2009

(54) HIGH-FREQUENCY KNIFE, ENDOSCOPIC APPARATUS, AND METHOD OF RESECTING LESIONED MUCOSAL PART USING HIGH-FREQUENCY KNIFE

(75) Inventors: Hiroyuki Ono, Sunto-gun (JP); Tsutomu Okada, Tachikawa (JP)

(73) Assignee: Olympus Corporation, Tokyo (JP)

( * ) Notice: Subject to any disclaimer, the term of this patent is extended or adjusted under 35 U.S.C. 154(b) by 558 days.

(21) Appl. No.: 10/959,642

(22) Filed: Oct. 6, 2004

(65) Prior Publication Data
US 2005/0072280 A1 Apr. 7, 2005

(30) Foreign Application Priority Data
Oct. 6, 2003 (JP) .............................. 2003-347311

(51) Int. Cl.
*A61B 18/18* (2006.01)
(52) U.S. Cl. .......................................... 606/45; 606/41
(58) Field of Classification Search .................... 606/41, 606/45–50, 113
See application file for complete search history.

(56) References Cited
U.S. PATENT DOCUMENTS

| | | | | |
|---|---|---|---|---|
| 4,493,320 A | * | 1/1985 | Treat | 606/47 |
| 4,976,711 A | * | 12/1990 | Parins et al. | 606/48 |
| 5,069,679 A | | 12/1991 | Taheri | |
| 5,078,716 A | * | 1/1992 | Doll | 606/47 |
| 5,171,255 A | * | 12/1992 | Rydell | 606/170 |
| 5,290,286 A | * | 3/1994 | Parins | 606/50 |
| 5,846,241 A | * | 12/1998 | Kittur et al. | 606/48 |
| 5,916,213 A | * | 6/1999 | Haissaguerre et al. | 606/41 |
| 5,961,526 A | * | 10/1999 | Chu et al. | 606/113 |
| 2001/0056248 A1 | | 12/2001 | Zimmon | |

FOREIGN PATENT DOCUMENTS

| | | |
|---|---|---|
| DE | 37 07 820 A1 | 9/1987 |
| JP | 4-329944 | 11/1992 |
| JP | 8-299355 | 11/1996 |

OTHER PUBLICATIONS

Koyama et al., "Increased Adaptation of Gastral-EMR: In View of Lesion Size—Manipulations for Excision of Entire Lesion, and Evaluation Results", Stomach and Intestines, vol. 37, No. 9, Aug. 2002, pp. 1155-1161.
Inoue et al., "Cap Method", Digestive Endoscope, vol. 14, No. 9, Sep. 2002, pp. 1301-1302.

\* cited by examiner

*Primary Examiner*—Michael Peffley
(74) *Attorney, Agent, or Firm*—Scully, Scott, Murphy & Presser, P.C.

(57) ABSTRACT

A high-frequency knife includes a cylindrical body member, electrically conductive axial member, operating section, and electrical insulating member. At least an outer peripheral surface of the body member has insulating properties. The axial member is inserted in the body member. A distal end portion of the axial member has a knife section. The operating section is provided on a proximal end portion of the axial member, can be actuated by a surgeon to project and retract the axial member with respect to the body member, and can supply electric power to the axial member. The insulating member is provided on the distal end of the axial member in a position at a distance from the distal end of the body member and has at least the longest axis of a cross section of the knife section.

21 Claims, 7 Drawing Sheets

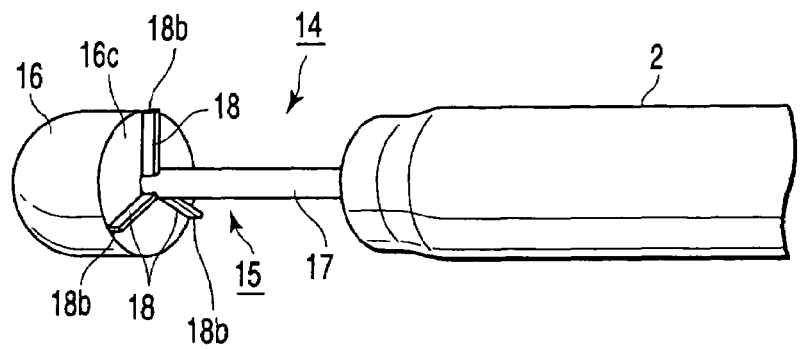
F I G. 8
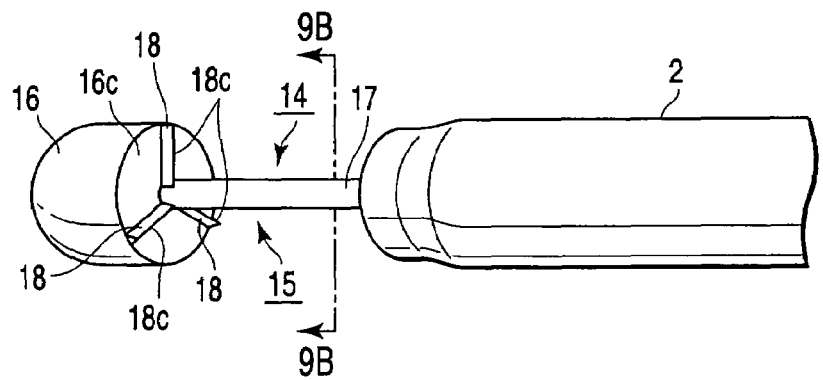
F I G. 9 A
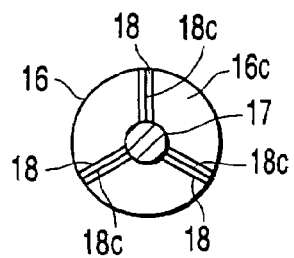
F I G. 9 B

HIGH-FREQUENCY KNIFE, ENDOSCOPIC
APPARATUS, AND METHOD OF RESECTING
LESIONED MUCOSAL PART USING
HIGH-FREQUENCY KNIFE

CROSS-REFERENCE TO RELATED
APPLICATIONS

This application is based upon and claims the benefit of priority from prior Japanese Patent Application No. 2003-347311, filed Oct. 6, 2003, the entire contents of which are incorporated herein by reference.

BACKGROUND OF THE INVENTION

1. Field of the Invention

The present invention relates to a high-frequency knife and an endoscopic apparatus for resecting, for example, organic tissues, and a method of resecting a lesioned mucosal part using the high-frequency knife.

2. Description of the Related Art

Procedures have conventionally been carried out to resect organic tissues, such as mucous membranes, endoscopically, for example. A high-frequency surgical instrument, such as the one described in Jpn. Pat. Appln. KOKAI Publication No. 4-329944, is used in these procedures.

The high-frequency surgical instrument described above has a needle-shaped knife section (electrode portion) that extends in its axial direction. If high-frequency current is supplied to the needle-shaped knife section, an organic tissue that is touched by the knife section can be cauterized and incised.

BRIEF SUMMARY OF THE INVENTION

According to one aspect of the present invention, there is provided a high-frequency knife, which includes a cylindrical body member, electrically conductive axial member, operating section, and electrical insulating member. At least an outer peripheral surface of the body member has insulating properties. The axial member is inserted in the body member. A distal end portion of the axial member has a knife section. The operating section is provided on a proximal end portion of the axial member, can be actuated by a surgeon to project and retract the axial member with respect to the body member, and can supply electric power to the axial member. The insulating member is provided on the distal end of the axial member in a position at a distance from the distal end of the body member and has at least the longest axis of a cross section of the knife section.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL
VIEWS OF THE DRAWING

The accompanying drawings, which are incorporated in and constitute a part of the specification, illustrate presently preferred embodiments of the invention, and together with the general description given above and the detailed description of the embodiments given below, serve to explain the principles of the invention.

FIG. 8 is a schematic perspective view showing a configuration of a distal end portion of a high-frequency knife and illustrating a knife section projecting from the distal end of a sheath according to a second embodiment;

FIG. 9A is a schematic perspective view showing a configuration of a distal end portion of a high-frequency knife and illustrating a knife section projecting from the distal end of a sheath according to a third embodiment;

FIG. 9B is a schematic partial sectional view taken along line 9B-9B of FIG. 9A according to a third embodiment;

DETAILED DESCRIPTION OF THE INVENTION

Several embodiments of the present invention will now be described with reference to the accompanying drawings.

A first embodiment will first be described with reference to FIGS. 1A to 7.

Figure 1A:
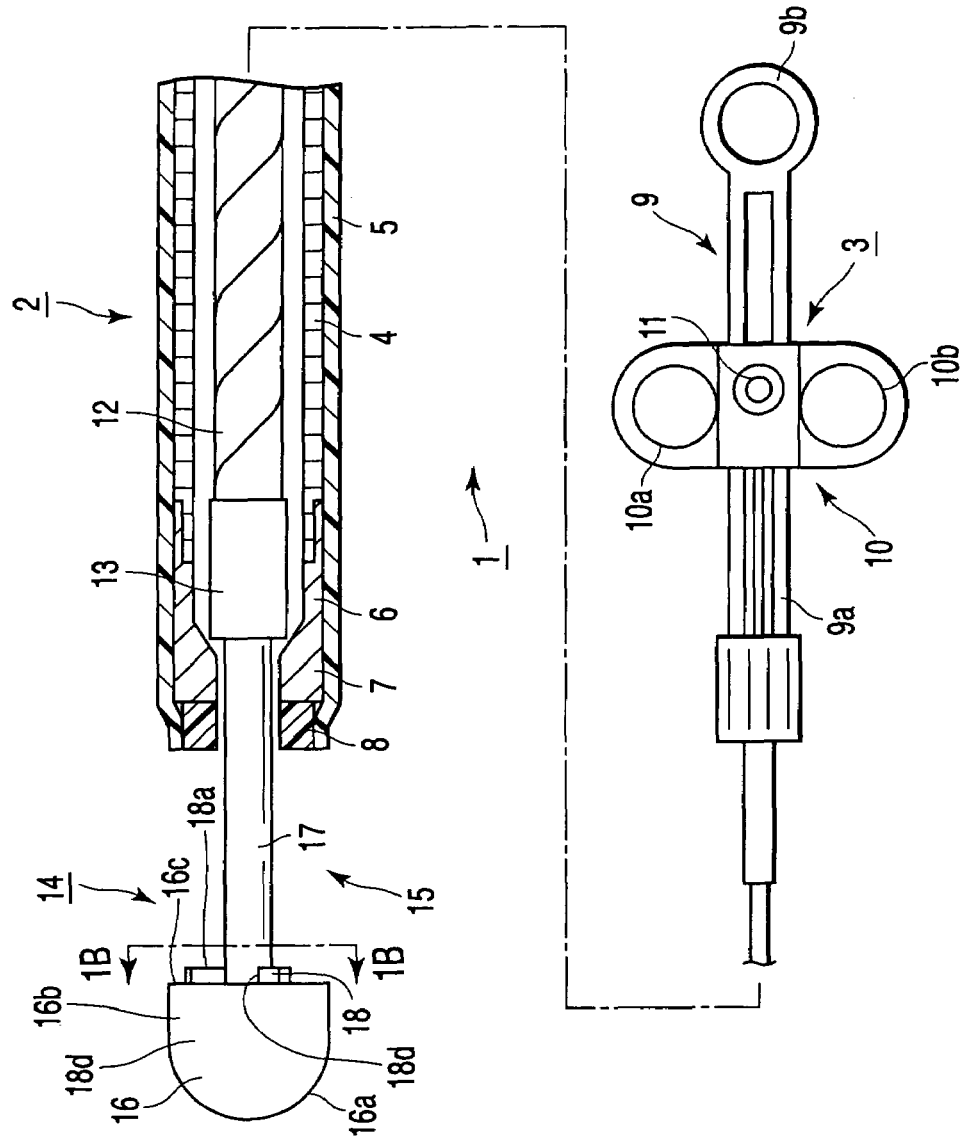
FIG. 1A is a schematic sectional view showing a configuration of a high-frequency knife and illustrating a knife section projecting from the distal end of a sheath according to a first embodiment.

As shown in FIG. 1A, a high-frequency knife 1 according to the embodiment includes a cylindrical sheath 2, for use as a body member of the knife 1, and a knife operating section 3.

The sheath 2 has flexibility and an outside diameter such that it can be passed through a channel (not shown) of an endoscope. The sheath 2 is provided mainly with a closely-wound coil 4 and an insulating tube 5, for example. The tube 5 covers the outer periphery of the coil 4. The tube 5 is formed of a resin material such as tetrafluoroethylene that has heat resistance and flexibility.

The insulating tube 5 has an outside diameter such that it can be passed through the channel of the endoscope. The closely-wound coil 4 has flexibility such that its shape can be easily changed as the shape of an insertion section of the endoscope changes with the sheath 2 in the channel of the endoscope.

A cylindrical stopper member 6 is coupled to the distal end of the closely-wound coil 4. The respective inner peripheral surfaces of junction parts of the coil 4 and the stopper member 6 are flush with each other, and so are their respective outer peripheral surfaces. The distal end portion of the stopper member 6 is formed having a thick-walled portion 7 such that its wall is thickened radially inward, as compared with the proximal end portion. A ring-shaped sheath end insulating tip 8 is located on the distal end side of the thick-walled portion 7. Preferably, the insulating tip 8 is formed of a ceramic material or some other material that has heat resistance. The inner peripheral surface of the insulating tip 8 is substantially flush with that of the thick-walled portion 7. The outer peripheral surface of the tip 8 is covered and held by the insulating tube 5.

The operating section 3 of the high-frequency knife 1 according to the embodiment is located on a surgeon's hand side with respect to the proximal end portion of the sheath 2. The operating section 3 is provided with an operating section body 9 and a manipulating slider 10 that is slidable with respect to the body 9. A linear guide shaft portion 9a is formed between the distal and proximal end portions of the operating section body 9. The slider 10 can slide straight along the guide shaft portion 9a between the end portions of the body 9.

The operating section body 9 has a thumb ring 9b at its proximal end portion. The manipulating slider 10 has finger rings 10a and 10b that are arranged at right angles to the axial direction of the body 9. Thus, the slider 10 can be slid with respect to the body 9 with a thumb in the ring 9b of the body 9 and index and middle fingers in the rings 10a and 10b, individually, for example. The slider 10 is provided with a connector portion 11, which is connected electrically with a cord (not shown) that leads to a high-frequency generator (not shown).

An electrically conductive operating wire 12 is passed through the sheath 2. The proximal end portion of the wire 12 is coupled to the slider 10 so as to be connected electrically to the connector portion 11. Thus, the operating wire 12 that is connected to the slider 10 can slide with respect to the operating section body 9. In contrast, an electrically conductive stopper receiving portion 13 is mounted on the distal end portion of the operating wire 12. The receiving portion 13 can abut against the thick-walled portion 7 of the stopper member 6.

The proximal end portion of a knife section 14 is connected to the stopper receiving portion 13. The knife section 14 is provided with an electrode 15 and an electrical insulator portion 16. The proximal end portion of the electrode 15 is connected to the stopper receiving portion 13. The electrical insulator portion 16 is provided on the distal end portion of the electrode 15.

The electrode 15 is provided with a first electrode portion 17 and second electrode portions 18. The first electrode portion 17 is in the form of a small-diameter rod having a diameter fixed throughout its length from the distal end portion to the proximal end portion, for example. The first electrode portion 17 can project in its axial direction from the distal end of the sheath 2. The second electrode portions 18 are provided on the distal end portion of the first electrode portion 17. The second electrode portions 18 extend radially from the first electrode portion 17 at right angles to the axial direction of the electrode portion 17.

The first electrode portion 17 is formed of an electrically conductive material, such as titanium alloy. The proximal end portion of the first electrode portion 17 is connected electrically to the stopper receiving portion 13. Therefore, the first electrode portion 17 is connected electrically to the connector portion 11 of the manipulating slider 10 by means of the stopper receiving portion 13 and the operating wire 12. As the operating wire 12 is advanced or retreated, the first electrode portion 17 moves along the axial direction of the sheath 2 in the bore of the sheath. Thus, the first electrode portion 17 can be projected or retracted from the distal end of the sheath 2.

Figure 1B:
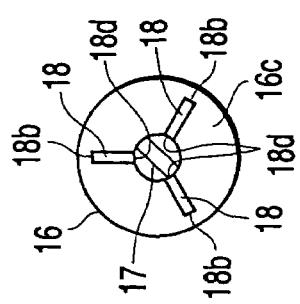
FIG. 1B is a schematic partial sectional view taken along line 1B-1B of FIG. 1A.

The second electrode portions 18 are formed integrally on the distal end of the first electrode portion 17. Like the first electrode portion 17, therefore, the second electrode portions 18 are formed of an electrically conductive material, such as titanium alloy. As shown in FIG. 1B, the second electrode portions 18 radially extend in three directions from the axis of the first electrode portion 17. The second electrode portions 18 have each same length. Thus, in the embodiment, the second electrode portions 18 are three in number. Each two adjacent second electrode portions 18 are located at an angle of 120° around the first electrode portion 17 from each other, in order to obtain similar operability in any position when the knife section 14 is rotated. Each of the second electrode portions 18 that extend from the first electrode portion 17 has a rectangular shape, e.g., an oblong shape.

The electrical insulator portion 16 is formed of a heat-resistant electrical insulating material, such as a ceramic material. As shown in FIG. 1A, the insulator portion 16 has a hemispherical distal end portion 16a and a substantially columnar (or substantially cylindrical) proximal end portion 16b that has the same outside diameter with the distal end portion 16a integrally. The respective distal end portions of the first and second electrode portions 17 and 18 are fixedly held or embedded in a proximal end face 16c of the proximal end portion 16b of the insulator portion 16. Thus, the second electrode portions 18 project from the proximal end face 16c of the proximal end portion 16b of the insulator portion 16 toward the distal end portion of the sheath 2. The first electrode portion 17 is fixed on the central axis of the proximal end portion 16b. In the embodiment, a radial end face 18b of each second electrode portion 18, its end remoter from the first electrode portion 17, and a fixed end 18d of each second electrode portion 18, which is fixed to the first electrode portion 17, project for the same length from the proximal end face 16c (mentioned later) of the insulator portion 16 toward the distal end portion of the sheath 2. The outside diameter of the proximal end portion 16b of the insulator portion 16 is greater than the length or distance from a holding portion (central axis of the insulator portion 16) on which the second electrode portions 18 are held to the end of each second electrode portion 18 remoter from the first electrode portion 17.

The following is a description of functions of the high-frequency knife 1 according to the embodiment. The procedure of the knife 1 will be described first.

The surgeon grasps the manipulating slider 10 and the operating section body 9 and moves the slider 10 rearward (or toward the proximal end) with respect to the body 9. Thereupon, the operating wire 12 moves rearward with respect to the sheath 2. Thus, the first electrode portion 17 is drawn into the sheath 2. In consequence, a proximal end face 18a of each second electrode portion 18 is caused to contact the insulating tip 8 on the distal end of the sheath 2 (see FIG. 2). In this state, the high-frequency knife 1 may be inserted into the channel of the endoscope with the knife section 14 non-operating, for example.

In contrast, the surgeon moves the slider 10 forward with the operating section body 9. Thereupon, the operating wire 12, along with the slider 10, moves forward with respect to the sheath 2. Thus, the first electrode portion 17 projects outward from the distal end of the sheath 2. In consequence, the proximal end face 18a of each second electrode portion 18 is caused to leave forward from the distal end of the sheath 2 (see FIGS. 1A and 3). In this state, the knife section 14 of the high-frequency knife 1 may be energized and manipulated to resect a mucous membrane, for example. The first electrode portion 17 (or the knife section 14) can project so that the stopper receiving portion 13 abuts against the thick-walled portion 7 of the stopper member 6 of the sheath 2.

Referring now to FIGS. 4 to 7, there will be described the procedure for endoscopically resecting a mucous membrane in a body cavity, for example. The high-frequency knife 1, which constitutes a part of an endoscopic apparatus, is used in combination with the endoscope.

The insertion section of the endoscope with the channel is inserted into a position near a lesioned region in the body cavity. A needle (not shown) is endoscopically introduced into the body cavity through the channel of the endoscope. The needle is used to inject a saline into a submucosa of a lesioned mucosal part 19, a target region to be resected in the body cavity, thereby swelling the lesioned part 19.

Figure 4:
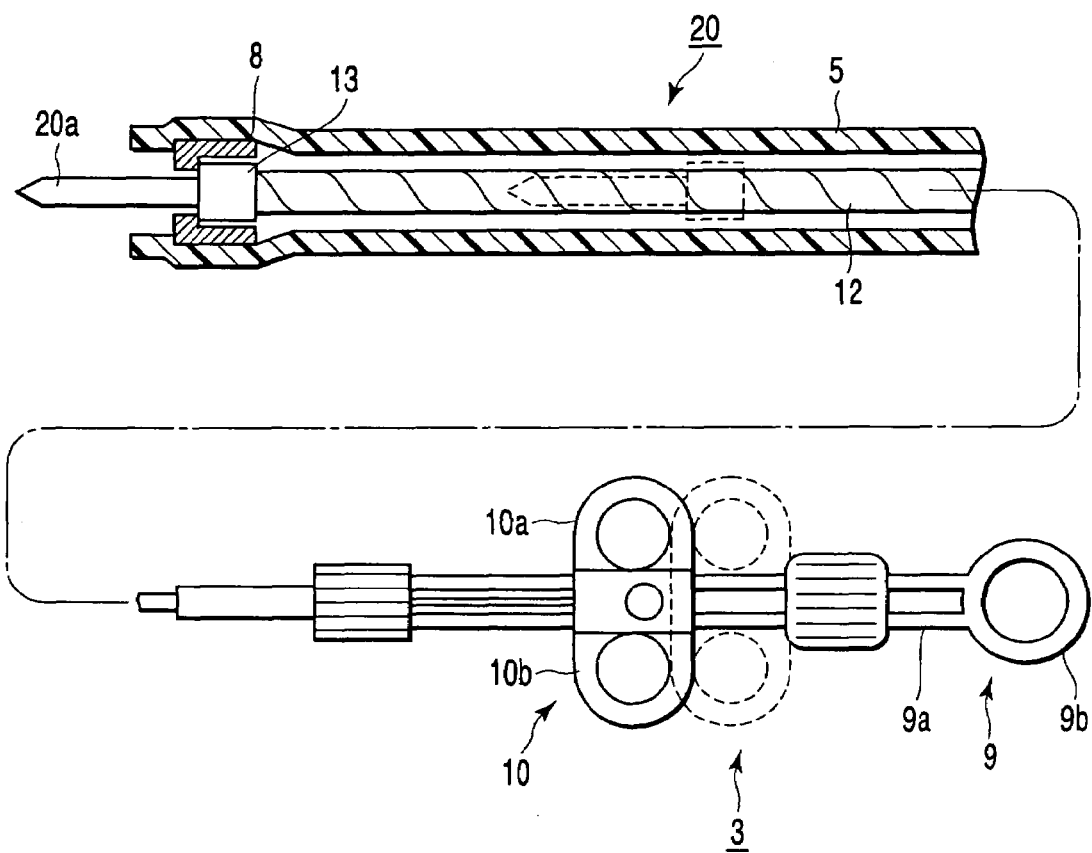
FIG. 4 is a schematic sectional view showing a configuration of another high-frequency knife for initial incision before use of the high-frequency knife and illustrating a knife section projecting from the distal end of a sheath according to the first embodiment.

Then, an unshown counter-electrode (patient plate) is attached to a patient's body. Thereafter, a high-frequency knife 20 (refer to Jpn. Pat. Appln. KOKAI Publication No. 4-329944, for example) having a needle-shaped electrode (knife section) 20a shown in FIG. 4 is also endoscopically introduced into the patient's body. The electrode 20a is energized for initial incision such that an opening 21 is bored in a part of a mucous membrane around the lesioned mucosal part 19 (see FIG. 5A). The knife 20 is drawn out of the channel of the endoscope.

Figure 2:
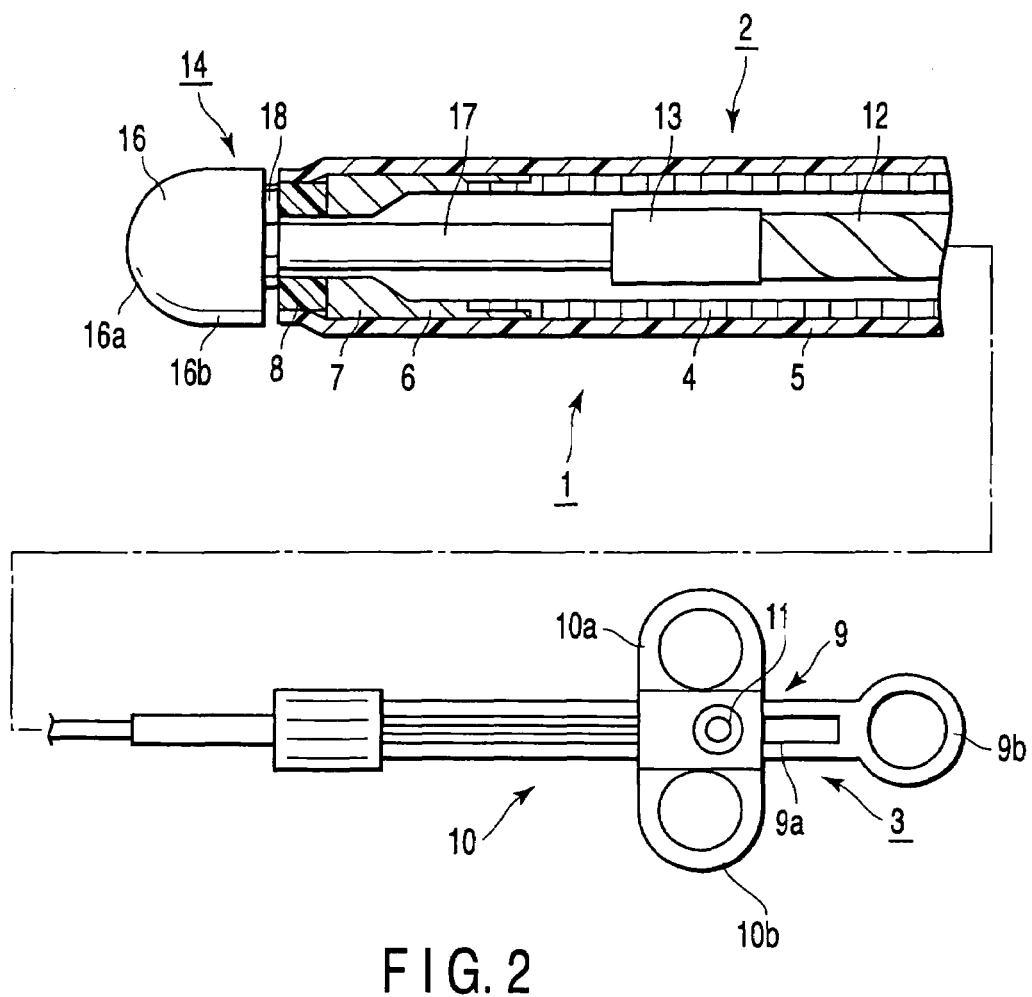
FIG. 2 is a schematic sectional view showing a configuration of the high-frequency knife and illustrating the knife section abutting against the distal end of the sheath according to the first embodiment.
Figure 3:
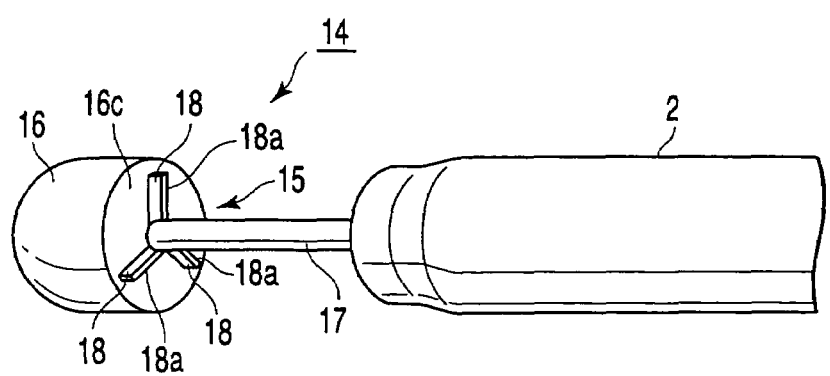
FIG. 3 is a schematic perspective view showing a configuration of a distal end portion of the high-frequency knife and illustrating the knife section projecting from the distal end of the sheath according to the first embodiment.

Subsequently, the high-frequency knife 1 according to the embodiment, having its first electrode portion 17 withdrawn in the sheath 2, is introduced into the body cavity through the evacuated channel of the endoscope, as shown in FIG. 2. The distal end portion of the knife 1 is projected from the distal end of the insertion section of the endoscope (see FIG. 5B). The manipulating slider 10 is slid with respect to the operating section body 9 so that the electrical insulator portion 16 is separated from the distal end of the sheath 2. The knife section 14 of the knife 1 is inserted into the initially incised opening 21 with its distal end portion (insulator portion 16) ahead (see FIG. 5C).

Figure 5A:
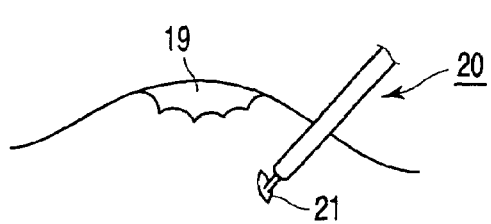
FIG. 5A is a schematic perspective view illustrating a process of resecting a lesioned mucosal part with use of the high-frequency knife according to the first embodiment.
Figure 5B:
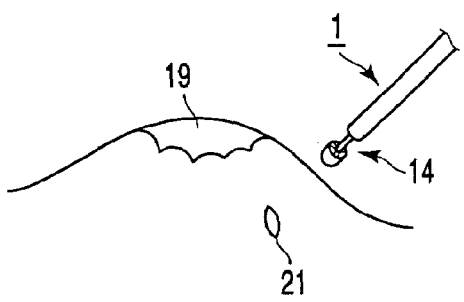
FIG. 5B is a schematic perspective view illustrating a lesion resecting process subsequent to the process shown in FIG. 5A according to the first embodiment.
Figure 5C:
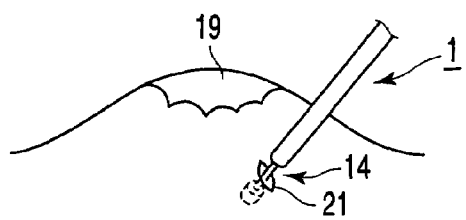
FIG. 5C is a schematic perspective view illustrating a lesion resecting process subsequent to the process shown in FIG. 5B according to the first embodiment.
Figure 5D:
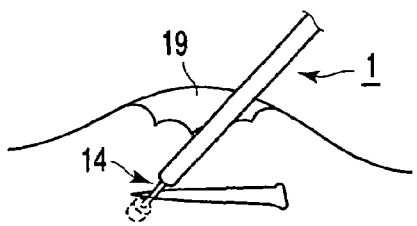
FIG. 5D is a schematic perspective view illustrating a lesion resecting process subsequent to the process shown in FIG. 5C according to the first embodiment.

Thereafter, high-frequency current is supplied to the electrode 15 (first and second electrode portions 17 and 18) of the knife section 14 of the high-frequency knife 1 as the knife section 14 is moved along a given direction of resection, as shown in FIG. 5D. If the knife section 14 is moved laterally, for example, the mucous membrane that touches the first electrode portion 17 is incised by it.

Figure 6:
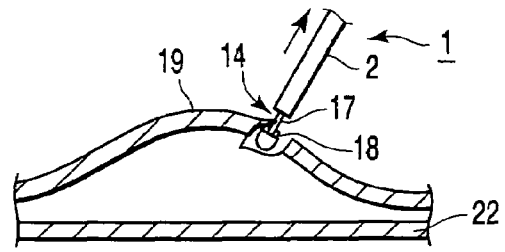
FIG. 6 is a schematic sectional view illustrating a process of resecting the lesioned mucosal part with use of the-high-frequency knife according to the first embodiment.

If the knife section 14 cannot be laterally moved with ease, its whole body is moved in its longitudinal direction (axial direction of the first electrode portion 17), as shown in FIG. 6. Thereupon, the mucous membrane that is hooked up by the second electrode portions 18 (electrical insulator portion 16) is incised as they touch them.

The knife section 14 of the high-frequency knife 1 is moved by combining this longitudinal movement and the aforementioned lateral movement. Thus, the region around the lesioned mucosal part 19 is incised circumferentially.

The distal end face of the knife section 14 (respective distal end portions of the second electrode portions 18) is covered by the electrical insulator portion 16. If the distal end of the knife section 14 is brought into contact with an unresectable tissue 22 (see FIG. 6) by its axial or longitudinal movement, the insulating effect of the insulator portion 16 prevents the high-frequency current that is supplied to the electrode 15 from flowing into the unresectable tissue 22. Thus, the surgeon need not take the trouble of moving the knife section 14 for a fixed depth such that the unresectable tissue 22 that is situated deep in the region to be resected can be prevented from being touched by that region (electrode 15) of the knife section 14 through which the high-frequency current flows.

Figure 7:
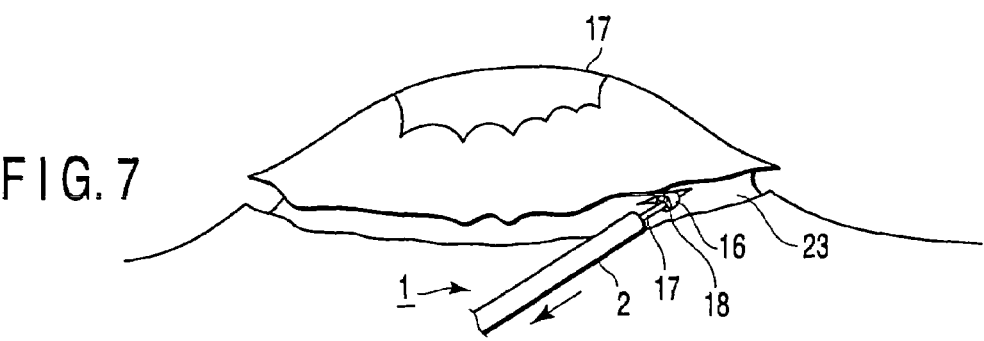
FIG. 7 is a schematic perspective view illustrating the way the lesioned mucosal part is resected with use of the high-frequency knife according to the first embodiment.

When the lesioned mucosal part 19 is fully incised in the circumferential direction in this manner, the first and second electrode portions 17 and 18 are held against a cut 23 around the lesioned mucosal part 19, and the lesioned part 19 is gradually incised and removed with the electrode portions 17 and 18 by combining the lateral and longitudinal movements of the high-frequency knife 1, as shown in FIG. 7. After the entire lesioned part 19 is resected and removed, the second electrode portions 18 of the knife section 14 of the knife 1 are caused to engage the distal end of the sheath 2, as shown in FIG. 2, and the knife 1 is drawn out of the channel of the endoscope toward the hand side. A grasping forceps (not shown) or the like is inserted into the evacuated channel of the endoscope and manipulated endoscopically to take out the lesioned mucosal part 19. Thereupon, the procedure is finished.

As described above, the high-frequency knife 1 according to the embodiment includes the sheath 2, first and second electrode portions 17 and 18, and electrical insulator portion 16. The sheath 2 serves as an electrically insulating body member. The first electrode portion 17 can be axially projected and retracted from the distal end of the sheath 2. The second electrode portions 18 are located on the distal end side of the first electrode portion 17 and radially extend at right angles to the axial direction of the first electrode portion 17. The insulator portion 16 is provided on the distal end side of the electrode portions 17 and 18 and has a diameter larger than that of the first electrode portion 17 at the least. In resecting the lesioned mucosal part 19, therefore, the tissue can be incised even when the knife section 14 is moved in various directions including the axial direction so that the mucous membrane can be hooked up by the second electrode portions 18, as well as when the knife section 14 moved laterally. Accordingly, possible movement directions for incision (degree of freedom in the direction of incision) are much more than in the case where the knife section 14 is provided with the first electrode portion 17 only.

Thus, the lesioned mucosal part 19 can be easily incised in various manners by using the high-frequency knife 1 according to the embodiment.

The high-frequency knife 1 according to the embodiment has the electrical insulator portion 16 on the distal end portion of the electrode 15. In incising the lesioned mucosal part 19, therefore, the surgeon need not take the trouble of advancing or retreating the knife section 14 within a fixed axial range such that the unresectable tissue 22 that is situated deep in the region to be resected can be prevented from being touched by the electrode 15 of the knife section 14. Thus, the procedure for incising the lesioned mucosal part 19 can be performed with ease.

In the embodiment, the second electrode portions 18 extend in three directions from the first electrode portion 17. Therefore, the area of contact between the lesioned mucosal part 19 and the second electrode portions 18 is so small that the output of the high-frequency current can be concentrated. Thus, the cutting quality of the second electrode portions 18 can be improved.

A second embodiment will now be described with reference to FIG. 8. This embodiment is a modification of the first embodiment. Therefore, like numerals are A used to designate like members of the first and second embodiments, and a detailed description of those members will be omitted in the following. The same applies to third to sixth embodiments, which will be mentioned later.

As shown in FIG. 8, second electrode portions 18 of a knife section 14 of a high-frequency knife 1 according to the embodiment extend at right angles to a first electrode portion 17. The second electrode portions 18 extend substantially to the same position as the side face (substantially columnar outer peripheral surface) of a proximal end portion 16b of an electrical insulator portion 16. For example, a radial end face 18b of each second electrode portion 18, its end remoter from the first electrode portion 17, is flush with the outer peripheral surface of the proximal end portion 16b of the insulator portion 16. The knife section 14 of the embodiment differs from the one (see FIG. 1A) described in connection with the first embodiment only in this point.

The high-frequency knife 1 according to the embodiment shares its functions with the one described in connection with the first embodiment, so that a repeated description of the functions will be omitted in the following.

As described above, the embodiment produces the following effects. A description of the effects that are shared by the high-frequency knife 1 according to the first embodiment will be omitted in the following.

The second electrode portions 18 of the knife section 14 extend substantially to the same position as the side face of the electrical insulator portion 16. Therefore, the second electrode portions 18 can incise the lesioned mucosal part 19 wider than in the case described in connection with the first embodiment. In removing the lesioned part 19, the respective radial end faces 18b of the second electrode portions 18 can incise it more securely.

A third embodiment will now be described with reference to FIGS. 9A and 9B.

As shown in FIGS. 9A and 9B, second electrode portions 18 of a knife section 14 of a high-frequency knife 1 according to the embodiment have their respective proximal end faces 18a formed as sharp ends 18c. More specifically, the cross section of each second electrode portion 18 is substantially triangular, that is, each electrode portion 18 is substantially in the shape of a triangular prism. The knife section 14 of the embodiment differs from the one (see FIG. 8) described in connection with the second embodiment only in this point.

The high-frequency knife 1 according to the embodiment shares its functions with the one (see FIG. 1A) described in connection with the first embodiment, so that a repeated description of the functions will be omitted in the following.

As described above, the embodiment produces the following effects. A description of the effects that are shared by the high-frequency knife 1 according to the second embodiment will be omitted in the following.

Since the second electrode portions 18 have their respective proximal end faces 18a sharper than those of the ones described in connection with the second embodiment, the cutting quality of the second electrode portions 18 that incise the tissue can be improved.

A fourth embodiment will now be described with reference to FIGS. 10A and 10B.

Figure 10A:
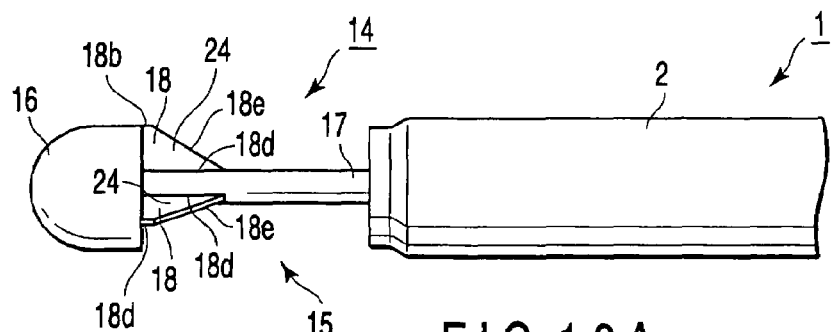
FIG. 10A is a schematic side view showing a configuration of a distal end portion of a high-frequency knife and illustrating a knife section projecting from the distal end of a sheath according to a fourth embodiment.
Figure 10B:
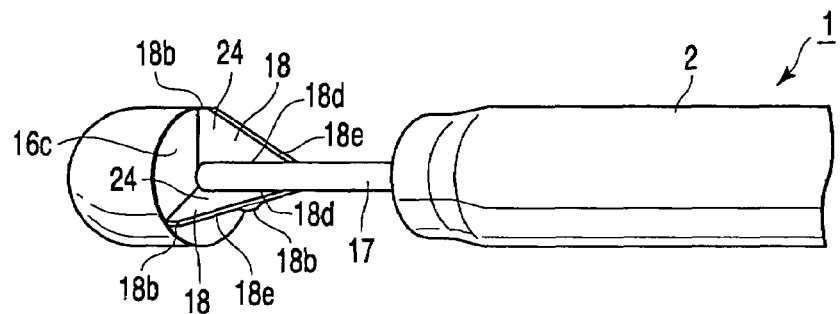
FIG. 10B is a schematic perspective view illustrating the knife section projecting from the distal end of the sheath according to a fourth embodiment.

As shown in FIGS. 10A and 10B, second electrode portions 18 of a knife section 14 of a high-frequency knife 1 according to the embodiment are in the form of wing portions 24 that radially extend in three directions perpendicular to the axial direction of a first electrode portion 17. A radial end face 18b of each second electrode portion 18 is shorter than its fixed end 18d on the side of the first electrode portion 17. Thus, a proximal end face (corresponding to the proximal end face 18a shown in FIG. 3) is in the form of a slope 18e that is defined between the radial end face 18b and the fixed end 18d. The knife section 14 of the embodiment differs from the one (see FIG. 8) described in connection with the second embodiment only in this point.

The following is a description of functions of the high-frequency knife 1 according to the embodiment. A repeated description of those functions which are shared by the high-frequency knife 1 (see FIG. 1A) described in connection with the first embodiment will be omitted in the following.

The lesioned mucosal part 19 can be incised and removed with the second electrode portions 18 held thereon even when the knife 1 is pulled even in an oblique direction intermediate between the lateral direction and the longitudinal direction (axial direction).

As described above, the embodiment produces the following effects. A description of the effects that are shared by the high-frequency knife 1 according to each of the foregoing embodiments will be omitted in the following.

The second electrode portions 18 of the knife section 14 are formed as the wing portions 24, which have the slopes 18e as their respective proximal end faces. Therefore, the lesioned mucosal part 19 can be incised and removed by pulling the knife obliquely, as well as in the lateral and axial directions. Thus, the efficiency of manipulation is improved.

A fifth embodiment will now be described with reference to FIGS. 11A and 11B.

Figure 11A:
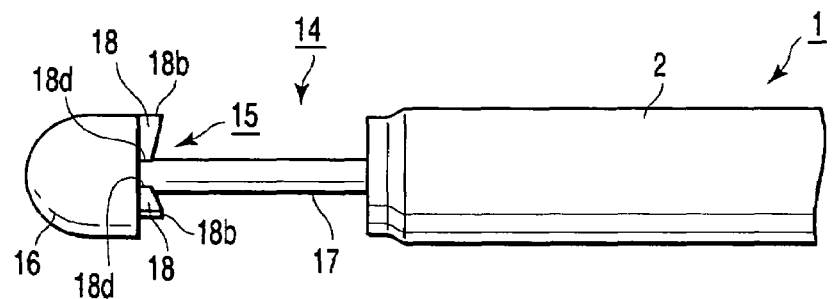
FIG. 11A is a schematic side view showing a configuration of a distal end portion of a high-frequency knife and illustrating a knife section projecting from the distal end of a sheath according to a fifth embodiment.
Figure 11B:
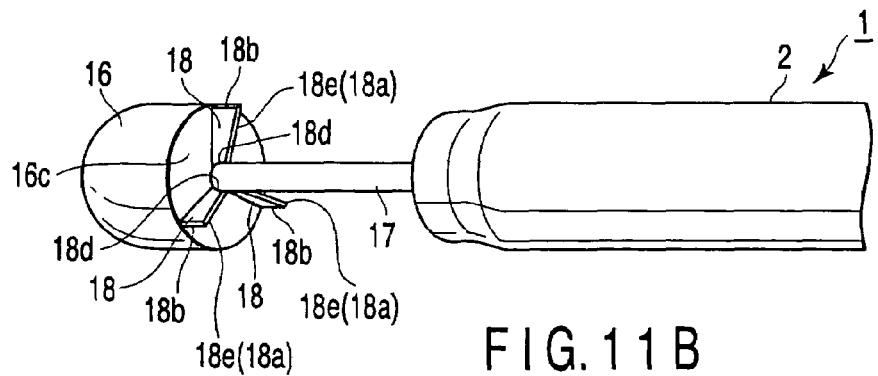
FIG. 11B is a schematic perspective view illustrating the knife section projecting from the distal end of the sheath according to a fifth embodiment.

As shown in FIGS. 11A and 11B, each second electrode portion 18 of a knife section 14 of a high-frequency knife 1 according to the embodiment has its radial end face 18b longer than its fixed end 18d on the side of the first electrode portion 17. Thus, the proximal end face 18a is in the form of a slope 18e that declines toward the center. The knife section 14 of the embodiment differs from the one (see FIG. 8) described in connection with the second embodiment only in this point.

The high-frequency knife 1 according to the embodiment shares its functions with the one (see FIG. 1A) described in connection with the first embodiment, so that a repeated description of the functions will be omitted in the following.

As described above, the embodiment produces the following effects. A description of the effects that are shared by the high-frequency knife 1 according to the second embodiment will be omitted in the following.

The proximal end face 18a of each second electrode portion 18 is the slope 18e that declines toward the center. Therefore, the second electrode portions 18 can incise and remove the lesioned mucosal part 19 with a good hitch.

A sixth embodiment will now be described with reference to FIGS. 12A and 12B.

Figure 12A:
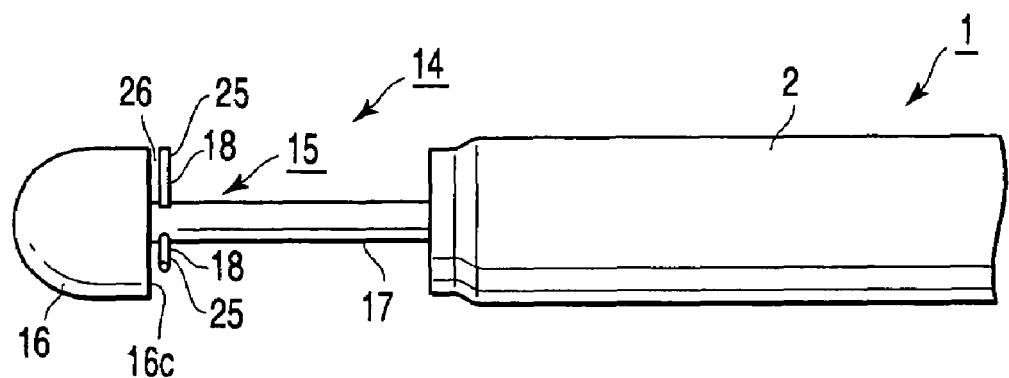
FIG. 12A is a schematic side view showing a configuration of a distal end portion of a high-frequency knife and illustrating a knife section projecting from the distal end of a sheath according to a sixth embodiment.
Figure 12B:
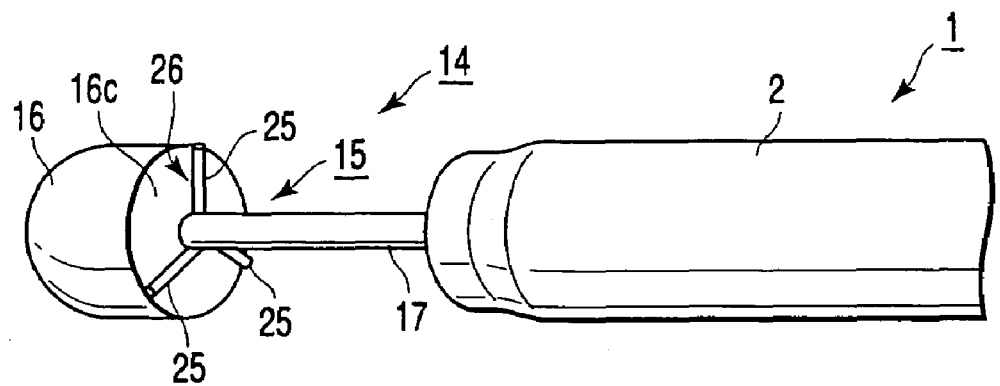
FIG. 12B is a schematic perspective view illustrating the knife section projecting from the distal end of the sheath according to the sixth embodiment.

As shown in FIGS. 12A and 12B, second electrode portions 18 of a knife section 14 of a high-frequency knife 1 according to the embodiment are in the form of rod portions 25 that radially extend in three directions perpendicular to the axial direction of a first electrode portion 17. The second electrode portions 18 are located at a narrow space 26 from a proximal end face 16c of an electrical insulator portion 16. The knife section 14 of the embodiment differs from the one (see FIG. 8) described in connection with the second embodiment only in this point.

The high-frequency knife 1 according to the embodiment shares its functions with the one (see FIG. 1A) described in connection with the first embodiment, so that a repeated description of the functions will be omitted in the following.

As described above, the embodiment produces the following effects. A description of the effects that are shared by the high-frequency knife 1 according to the second embodiment will be omitted in the following.

The second electrode portions 18 are in the form of the rod portions 25. They are situated at the space 26 from the proximal end face 16c of the electrical insulator portion 16. Therefore, the area of contact between the lesioned mucosal part 19 and the second electrode portions 18 is so small that the output of the high-frequency current can be concentrated. Thus, the cutting quality of the second electrode portions 18 can be improved.

In the first to sixth embodiments, the second electrode portions 18 have been described as being three in number. Alternatively, however, they may be located extending in four or five directions, for example. Preferably, in this case, the second electrode portions 18 should be arranged at equal angles to one another around the first electrode portion 17. In this way, steady availability can be enjoyed even when the knife section 14 is rotated around its axis.

The second electrode portions 18 of the same knife section 14 described in connection with each of the first to sixth embodiments need not always be of the same shape, and different shapes may be suitably combined for them. For example, the second electrode portions 18 according to the first embodiment (see FIG. 3), second embodiment (see FIG. 8), and third embodiment (see FIG. 9A) may be suitably combined to form a triple structure.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A monopolar high-frequency knife comprising:
   a cylindrical body member of which at least an outer peripheral surface has insulating properties;
   a monopolar electrode, the monopolar electrode being an electrically conductive axial member inserted in the body member and having a distal end portion of which the length of projection from a distal end of the body member is adjustable and a proximal end portion which operates together with the distal end portion, the distal end portion having a knife section thereon;
   an operating section which is provided on the proximal end portion of the axial member, is able to be actuated by a surgeon to project and retract the axial member with respect to the body member, and is able to supply electric power to the axial member; and
   an electrical insulating member which is provided on the distal end of the axial member in a position at a distance from the distal end of the body member and has at least the longest axis of a cross section of the knife section;
   wherein the knife section includes:
   a first electrode portion which is able to be projected and retracted from the distal end of the body member, and
   a plurality of second electrode portions which extend at right angles to at least the axial direction of the first electrode portion from the distal end portion of the first electrode portion and are able to approach and leave the distal end of the body member;
   wherein the plurality of second electrode portions are electrically connected to each other and to the first electrode portion; and
   wherein the second electrode portions extend for the same length from a central axis of the first electrode portion,
   the electrical insulating member has a radius including at least the extended longest length of each second electrode portion from the central axis of the first electrode portion and is provided on a distal end of the first electrode portion, and
   the second electrode portions are arranged between the distal end of the body member and the electrical insulating member.

2. A high-frequency knife according to claim 1, wherein the second electrode portions extend in at least three directions from the distal end portion of the first electrode portion.

3. A high-frequency knife according to claim 1,
   wherein the electrical insulating member has a proximal-end-side end face located close to the distal end of the body member, and
   the second electrode portions are covered at least partially by the proximal-end-side end face.

4. A high-frequency knife according to claim 1,
   wherein the electrical insulating member has a proximal-end-side end face located close to the distal end of the body member, and
   the second electrode portions are located in a position at a distance from the proximal-end-side end face of the electrical insulating member.

5. A monopolar high-frequency knife comprising:
   a cylindrical body member of which at least an outer peripheral surface has insulating properties;
   a monopolar electrode, the monopolar electrode being an electrically conductive axial member inserted in the body member and having a distal end portion of which the length of projection from a distal end of the body member is adjustable and a proximal end portion which operates together with the distal end portion, the distal end portion having a knife section thereon;
   an operating section which is provided on the proximal end portion of the axial member, is able to be actuated by a surgeon to project and retract the axial member with respect to the body member, and is able to supply electric power to the axial member; and
   an electrical insulating member which is provided on the distal end of the axial member in a position at a distance from the distal end of the body member and has at least the longest axis of a cross section of the knife section;

wherein the knife section includes:

a first electrode portion which is able to be projected and retracted from the distal end of the body member, and a plurality of second electrode portions which extend at right angles to at least the axial direction of the first electrode portion from the distal end portion of the first electrode portion and are able to approach and leave the distal end of the body member;

wherein the plurality of second electrode portions are electrically connected to each other and to the first electrode portion; and wherein each of the second electrode portions has a sharp body-member-side end portion on the side nearer to the distal end portion of the body member.

6. A monopolar high-frequency knife comprising:

a cylindrical body member of which at least an outer peripheral surface has insulating properties;

a monopolar electrode, the monopolar electrode being an electrically conductive axial member inserted in the body member and having a distal end portion of which the length of projection from a distal end of the body member is adjustable and a proximal end portion which operates together with the distal end portion, the distal end portion having a knife section thereon;

an operating section which is provided on the proximal end portion of the axial member, is able to be actuated by a surgeon to project and retract the axial member with respect to the body member, and is able to supply electric power to the axial member; and an electrical insulating member which is provided on the distal end of the axial member in a position at a distance from the distal end of the body member and has at least the longest axis of a cross section of the knife section;

wherein the knife section includes:

a first electrode portion which is able to be projected and retracted from the distal end of the body member, and a plurality of second electrode portions which extend at right angles to at least the axial direction of the first electrode portion from the distal end portion of the first electrode portion and are able to approach and leave the distal end of the body member;

wherein the plurality of second electrode portions are electrically connected to each other and to the first electrode portion; and wherein each of the second electrode portions has a fixed end fixed to the first electrode portion and a radial end at a distance from the fixed end, the radial end including a slope portion inclined in a direction perpendicular to the axial direction of the first electrode portion.

7. A monopolar high-frequency knife comprising:

a cylindrical body member of which at least an outer peripheral surface has insulating properties;

a monopolar electrode, the monopolar electrode being an electrically conductive axial member inserted in the body member and having a distal end portion of which the length of projection from a distal end of the body member is adjustable and a proximal end portion which operates together with the distal end portion, the distal end portion having a knife section thereon;

an operating section which is provided on the proximal end portion of the axial member, is able to be actuated by a surgeon to project and retract the axial member with respect to the body member, and is able to supply electric power to the axial member; and an electrical insulating member which is provided on the distal end of the axial member in a position at a distance from the distal end of the body member and has at least the longest axis of a cross section of the knife section;

wherein the knife section includes:

a first electrode portion which is able to be projected and retracted from the distal end of the body member, and a plurality of second electrode portions which extend at right angles to at least the axial direction of the first electrode portion from the distal end portion of the first electrode portion and are able to approach and leave the distal end of the body member;

wherein the plurality of second electrode portions are electrically connected to each other and to the first electrode portion; and wherein each of the second electrode portions has a fixed end fixed to the first electrode portion and a radial end at a distance from the fixed end, the radial end being shorter than the fixed end.

8. A monopolar high-frequency knife comprising:

a cylindrical body member of which at least an outer peripheral surface has insulating properties;

a monopolar electrode, the monopolar electrode being an electrically conductive axial member inserted in the body member and having a distal end portion of which the length of projection from a distal end of the body member is adjustable and a proximal end portion which operates together with the distal end portion, the distal end portion having a knife section thereon;

an operating section which is provided on the proximal end portion of the axial member, is able to be actuated by a surgeon to project and retract the axial member with respect to the body member, and is able to supply electric power to the axial member; and an electrical insulating member which is provided on the distal end of the axial member in a position at a distance from the distal end of the body member and has at least the longest axis of a cross section of the knife section;

wherein the knife section includes:

a first electrode portion which is able to be projected and retracted from the distal end of the body member, and a plurality of second electrode portions which extend at right angles to at least the axial direction of the first electrode portion from the distal end portion of the first electrode portion and are able to approach and leave the distal end of the body member;

wherein the plurality of second electrode portions are electrically connected to each other and to the first electrode portion; and wherein the electrical insulating member has a proximal-end-side end face located close to the distal end of the body member, and each of the second electrode portions has a fixed end fixed to the first electrode portion, a radial end at a distance from the fixed end, and a slope portion at a distance from the proximal-end-side end face.

9. A monopolar high-frequency knife comprising:

an elongated cylindrical body member of which at least an outer peripheral surface has electrical insulating properties;

a first electrode portion electrically connected to the elongated cylindrical body member and which has an axial distal end portion and is able to move along the axial direction of the body member inside the body member so as to be projected and retracted from the distal end of the body member;

a plurality of second electrode portions which extend at right angles to at least the axial direction of the first electrode portion from the distal end portion of the first electrode portion; and an electrical insulator which is provided on the distal end portion of the first electrode portion and has at least one of a diameter and diagonal line longer than the line of a cross section of the distal end portion of the first electrode portion, wherein the plurality of second electrode portions are electrically connected to each other and to the first electrode portion; and wherein the second electrode portions extend in at least three directions from the distal end portion of the first electrode portion.

10. A monopolar high-frequency knife comprising:

an elongated cylindrical body member of which at least an outer peripheral surface has electrical insulating properties;

a first electrode portion electrically connected to the elongated cylindrical body member and which has an axial distal end portion and is able to move along the axial direction of the body member inside the body member so as to be projected and retracted from the distal end of the body member;

a plurality of second electrode portions which extend at right angles to at least the axial direction of the first electrode portion from the distal end portion of the first electrode portion; and an electrical insulator which is provided on the distal end portion of the first electrode portion and has at least one of a diameter and diagonal line longer than the line of a cross section of the distal end portion of the first electrode portion, wherein the plurality of second electrode portions are electrically connected to each other and to the first electrode portion; and wherein the second electrode portions extend for the same length from a central axis of the first electrode portion, the electrical insulator has a radius including at least the extended longest length of each second electrode portion from the central axis of the first electrode portion and is provided on a distal end of the first electrode portion, and the second electrode portions are arranged between the distal end of the body member and the electrical insulator.

11. A high-frequency knife according to claim 10, wherein the electrical insulator has a proximal-end-side end face located close to the distal end of the body member, and the second electrode portions are covered at least partially by the proximal-end-side end face.

12. A high-frequency knife according to claim 10, wherein the electrical insulator has a proximal-end-side end face located close to the distal end of the body member, and the second electrode portions are located in a position at a distance from the proximal-end-side end face of the electrical insulating member.

13. A monopolar high-frequency knife comprising:

an elongated cylindrical body member of which at least an outer peripheral surface has electrical insulating properties;

a first electrode portion electrically connected to the elongated cylindrical body member and which has an axial distal end portion and is able to move along the axial direction of the body member inside the body member so as to be projected and retracted from the distal end of the body member;

a plurality of second electrode portions which extend at right angles to at least the axial direction of the first electrode portion from the distal end portion of the first electrode portion; and an electrical insulator which is provided on the distal end portion of the first electrode portion and has at least one of a diameter and diagonal line longer than the line of a cross section of the distal end portion of the first electrode portion, wherein the plurality of second electrode portions are electrically connected to each other and to the first electrode portion; and wherein each of the second electrode portions has a sharp body-member-side end portion on the side nearer to the distal end portion of the body member.

14. A monopolar high-frequency knife comprising:

an elongated cylindrical body member of which at least an outer peripheral surface has electrical insulating properties;

a first electrode portion electrically connected to the elongated cylindrical body member and which has an axial distal end portion and is able to move along the axial direction of the body member inside the body member so as to be projected and retracted from the distal end of the body member;

a plurality of second electrode portions which extend at right angles to at least the axial direction of the first electrode portion from the distal end portion of the first electrode portion; and an electrical insulator which is provided on the distal end portion of the first electrode portion and has at least one of a diameter and diagonal line longer than the line of a cross section of the distal end portion of the first electrode portion, wherein the plurality of second electrode portions are electrically connected to each other and to the first electrode portion; and wherein each of the second electrode portions has a fixed end fixed to the first electrode portion and a radial end at a distance from the fixed end, the radial end including a slope portion inclined in a direction perpendicular to the axial direction of the first electrode portion.

15. A monopolar high-frequency knife comprising:

an elongated cylindrical body member of which at least an outer peripheral surface has electrical insulating properties;

a first electrode portion electrically connected to the elongated cylindrical body member and which has an axial distal end portion and is able to move alone the axial direction of the body member inside the body member so as to be projected and retracted from the distal end of the body member;

a plurality of second electrode portions which extend at right angles to at least the axial direction of the first electrode portion from the distal end portion of the first electrode portion; and an electrical insulator which is provided on the distal end portion of the first electrode portion and has at least one of a diameter and diagonal line longer than the line of a cross section of the distal end portion of the first electrode portion, wherein the plurality of second electrode portions are electrically connected to each other and to the first electrode portion; and wherein each of the second electrode portions has a fixed end fixed to the first electrode portion and a radial end at a distance from the fixed end, the radial end being longer than the fixed end.

16. A monopolar high-frequency knife comprising:

an elongated cylindrical body member of which at least an outer peripheral surface has electrical insulating properties;

a first electrode portion electrically connected to the elongated cylindrical body member and which has an axial distal end portion and is able to move along the axial direction of the body member inside the body member so as to be projected and retracted from the distal end of the body member;

a plurality of second electrode portions which extend at right angles to at least the axial direction of the first electrode portion from the distal end portion of the first electrode portion; and an electrical insulator which is provided on the distal end portion of the first electrode portion and has at least one of a diameter and diagonal line longer than the line of a cross section of the distal end portion of the first electrode portion, wherein the plurality of second electrode portions are electrically connected to each other and to the first electrode portion; and wherein each of the second electrode portions has a fixed end fixed to the first electrode portion and a radial end at a distance from the fixed end, the radial end being shorter than the fixed end.

17. A monopolar high-frequency knife comprising:

an elongated cylindrical body member of which at least an outer peripheral surface has electrical insulating properties;

a first electrode portion electrically connected to the elongated cylindrical body member and which has an axial distal end portion and is able to move along the axial direction of the body member inside the body member so as to be projected and retracted from the distal end of the body member;

a plurality of second electrode portions which extend at right angles to at least the axial direction of the first electrode portion from the distal end portion of the first electrode portion; and an electrical insulator which is provided on the distal end portion of the first electrode portion and has at least one of a diameter and diagonal line longer than the line of a cross section of the distal end portion of the first electrode portion, wherein the plurality of second electrode portions are electrically connected to each other and to the first electrode portion; and wherein the electrical insulator has a proximal-end-side end face located close to the distal end of the body member, and each of the second electrode portions has a fixed end fixed to the first electrode portion, a radial end at a distance from the fixed end, and a slope portion at a distance from the proximal-end-side end face.

18. An endoscopic apparatus comprising:

an endoscope having a channel;

a cylindrical body member which is able to be inserted into the channel and of which at least an outer peripheral surface has insulating properties;

a monopolar electrode, the monopolar electrode being an electrically conductive axial member inserted in the body member and having a distal end portion of which the length of projection from a distal end of the body member is adjustable and a proximal end portion which operates together with the distal end portion, the distal end portion having a knife section thereon;

an operating section which is provided on the proximal end portion of the axial member, is able to be actuated by a surgeon to project and retract the axial member with respect to the body member, and is able to supply electric power to the axial member; and an electrical insulating member which is provided on the distal end of the axial member in a position at a distance from the distal end of the body member and has at least the longest axis of a cross section of the knife section;

wherein the knife section includes:

a first electrode portion which is able to be projected and retracted from the distal end of the body member, and a plurality of second electrode portions which extend at right angles to at least the axial direction of the first electrode portion from the distal end portion of the first electrode portion and are able to approach and leave the distal end of the body member;

wherein the plurality of second electrode portions are electrically connected to each other and to the first electrode portion; and wherein the second electrode portions extend in at least three directions from the distal end portion of the first electrode portion.

19. A method of resecting a lesioned mucosal part using a monopolar high-frequency knife, comprising:

swelling the lesioned mucosal part by endoscopically injecting a saline solution into a submucosa of the lesioned mucosal part;

carrying out initial incision such that an opening is endoscopically bored in a part of a mucous membrane around the lesioned mucosal part;

endoscopically inserting a monopolar high-frequency knife having an electrical insulating member into a distal end of an axial member having a knife section on a distal end portion thereof; and incising a region around the lesioned mucosal part in the circumferential direction thereof with the knife section inserted into the opening and energized;

wherein the step of incising a region around the lesioned mucosal part in the circumferential direction thereof with the knife section inserted into the opening and energized includes:

incising the mucous membrane in contact with a first electrode portion of the knife section having the first electrode portion, which is provided on the proximal end portion side of the knife section and is able to be projected and retracted from a distal end of a body member, and a plurality of second electrode portions, which extend at right angles to at least the axial direction of the first electrode portion from a distal end of the first electrode portion and are able to approach and leave the distal end of the body member; and electrically connecting the plurality of second electrode portions to each other and to the first electrode portion.

20. A method of resecting a lesioned mucosal part using a high-frequency knife according to claim 19, which further includes incising the mucous membrane brought into contact with the second electrode portions of the knife section and hooked up.

21. A method of resecting a lesioned mucosal part using a monopolar high-frequency knife, comprising:

swelling the lesioned mucosal part by endoscopically injecting a saline solution into a submucosa of the lesioned mucosal part;

carrying out initial incision such that an opening is endoscopically bored in a part of a mucous membrane around the lesioned mucosal part;

endoscopically inserting a monopolar high-frequency knife having an electrical insulating member into a distal end of an axial member having a knife section on a distal end portion thereof; and incising a region around the lesioned mucosal part in the circumferential direction thereof with the knife section inserted into the opening and energized;

wherein the step of incising a region around the lesioned mucosal part in the circumferential direction thereof with the knife section inserted into the opening and energized includes:

incising the mucous membrane in contact with a plurality of second electrode portions of the knife section having a first electrode portion, which is provided on the proximal end portion side of the knife section and is able to be projected and retracted from a distal end of a body member, and the second electrode portions, which extend at right angles to at least the axial direction of the first electrode portion from a distal end of the first electrode portion and are able to approach and leave the distal end of the body member, and hooked up.

* * * * *